United States Patent
Sander

(10) Patent No.: US 9,949,839 B2
(45) Date of Patent: Apr. 24, 2018

(54) REVISION IMPLANT AUGMENTS, SYSTEMS, AND METHODS

(71) Applicant: Wright Medical Technology, Inc., Arlington, TN (US)

(72) Inventor: Elizabeth Sander, Memphis, TN (US)

(73) Assignee: Wright Medical Technology, Inc., Memphis, TN (US)

( * ) Notice: Subject to any disclaimer, the term of this patent is extended or adjusted under 35 U.S.C. 154(b) by 83 days.

(21) Appl. No.: 13/800,838

(22) Filed: Mar. 13, 2013

(65) Prior Publication Data
US 2014/0277538 A1 Sep. 18, 2014

(51) Int. Cl.
A61F 2/30 (2006.01)
A61F 2/42 (2006.01)
A61F 2/46 (2006.01)

(52) U.S. Cl.
CPC ........ *A61F 2/4202* (2013.01); *A61F 2/30734* (2013.01); *A61F 2/4637* (2013.01);
(Continued)

(58) Field of Classification Search
CPC ............... A61F 2/42; A61F 2/4202; A61F 2002/30121; A61F 2002/3013; A61F 2002/30136; A61F 2002/30169; A61F 2002/30191; A61F 2002/30299; A61F 2002/30329; A61F 2002/30599; A61F 2002/3079; A61F 2002/4205; A61F 2002/4207; A61F 2002/421; A61F 2/389; A61F 2/3859; A61F 2/38; A61F 2/3804; A61F 2002/2807; A61F 2002/281; A61F 2002/2825; A61F 2002/2828;
(Continued)

(56) References Cited

U.S. PATENT DOCUMENTS 1,090,881 A 3/1914 Rowley
3,872,519 A 3/1975 Giannestras et al.
(Continued)

FOREIGN PATENT DOCUMENTS

CN 1753651 A 3/2006
CN 203001181 U 6/2013
(Continued)

OTHER PUBLICATIONS

InBone II Total Ankle System. Verified by the Wayback Machine Dec. 24, 2011. http://www.wmt.com/footandankle/FA701-1210.asp.*

(Continued)

*Primary Examiner* — Thomas J Sweet
*Assistant Examiner* — Christie Bahena
(74) *Attorney, Agent, or Firm* — Duane Morris LLP

(57) ABSTRACT

In some embodiments, a surgical method includes creating an incision in a patient, exposing a multi-component prosthesis implanted in a patient, disassembling at least one component of the multi-component prosthesis, and coupling a first revision implant component to a first component of the multi-component prosthesis. The revision implant component has a body including at least one of a projection or an opening that is complementary to a feature of the first component of the multi-component prosthesis for coupling the revision implant component to the first component of the multi-component prosthesis.

7 Claims, 15 Drawing Sheets

(52) U.S. Cl.
CPC .............. *A61F 2002/30331* (2013.01); *A61F 2002/30383* (2013.01); *A61F 2002/30405* (2013.01); *A61F 2002/30426* (2013.01); *A61F 2002/30433* (2013.01); *A61F 2002/30599* (2013.01); *A61F 2002/30604* (2013.01); *A61F 2002/30736* (2013.01); *A61F 2002/4205* (2013.01); *A61F 2002/4207* (2013.01)

(58) Field of Classification Search
CPC ........ A61F 2002/2832; A61F 2002/285; A61F 2002/2853; A61F 2002/2871; A61F 2002/2875; A61F 2002/2878; A61F 2002/2882; A61F 2002/2885; A61F 2002/2889; A61F 2002/2892; A61F 2002/2896; A61F 2002/30331; A61F 2002/30345; A61F 2002/30504; A61F 2002/30611; A61F 2002/30652; A61F 2002/30736; A61F 2002/30724; A61F 2002/3082; A61F 2002/30835; A61F 2/2814; A61F 2/30; A61B 17/17032
USPC ......... 623/18.11, 20.23, 21.18, 23.25, 23.28, 623/23.45
See application file for complete search history.

(56) References Cited

U.S. PATENT DOCUMENTS

| | | | |
|---|---|---|---|
| 3,889,300 | A | 6/1975 | Smith |
| 3,896,502 | A | 7/1975 | Lennox |
| 3,896,503 | A | 7/1975 | Freeman et al. |
| 3,975,778 | A | 8/1976 | Newton, III |
| 3,987,500 | A | 10/1976 | Schlein |
| 4,156,944 | A * | 6/1979 | Schreiber et al. ......... 623/21.18 |
| 4,166,292 | A | 9/1979 | Bokros et al. |
| 4,229,839 | A | 10/1980 | Schwemmer |
| 4,232,404 | A | 11/1980 | Samuelson et al. |
| 4,553,273 | A | 11/1985 | Wu |
| 4,676,797 | A | 6/1987 | Anapliotis et al. |
| 4,713,003 | A * | 12/1987 | Symington .......... A61C 8/0022 433/173 |
| 4,822,364 | A * | 4/1989 | Inglis .................... A61F 2/3804 623/20.12 |
| 4,827,496 | A | 5/1989 | Cheney |
| 5,041,139 | A | 8/1991 | Branemark |
| 5,326,365 | A | 7/1994 | Alvine |
| 5,397,360 | A | 3/1995 | Cohen et al. |
| 5,766,259 | A | 6/1998 | Sammarco |
| 5,824,106 | A | 10/1998 | Fournol |
| 6,102,956 | A | 8/2000 | Kranz |
| 6,110,172 | A * | 8/2000 | Jackson ............. A61B 17/7032 606/305 |
| 6,136,032 | A | 10/2000 | Viladot Perice et al. |
| 6,139,584 | A | 10/2000 | Ochoa et al. |
| 6,168,631 | B1 | 1/2001 | Maxwell et al. |
| 6,488,712 | B1 | 12/2002 | Tournier et al. |
| 6,589,281 | B2 | 7/2003 | Hyde, Jr. |
| 6,663,669 | B1 | 12/2003 | Reiley |
| 6,699,290 | B1 * | 3/2004 | Wack .................... A61F 2/3804 623/19.13 |
| 6,875,236 | B2 | 4/2005 | Reiley |
| 6,926,739 | B1 | 8/2005 | O'Connor et al. |
| 7,534,246 | B2 | 5/2009 | Reiley et al. |
| 8,512,412 | B2 | 8/2013 | Hanson et al. |
| 8,715,362 | B2 | 5/2014 | Reiley et al. |
| 2002/0055744 | A1 | 5/2002 | Reiley |
| 2002/0095214 | A1 | 7/2002 | Hyde, Jr. |
| 2002/0115742 | A1 | 8/2002 | Trieu et al. |
| 2003/0149485 | A1 * | 8/2003 | Tornier ................... 623/18.11 |
| 2003/0204263 | A1 | 10/2003 | Justin et al. |
| 2004/0102854 | A1 * | 5/2004 | Zhu .................... A61F 2/30734 623/23.15 |
| 2004/0122440 | A1 | 6/2004 | Daniels et al. |
| 2004/0167629 | A1 * | 8/2004 | Geremakis ............ A61F 2/4014 623/19.14 |
| 2004/0172138 | A1 | 9/2004 | May et al. |
| 2004/0193278 | A1 | 9/2004 | Maroney et al. |
| 2005/0049711 | A1 | 3/2005 | Ball |
| 2005/0192673 | A1 | 9/2005 | Saltzman et al. |
| 2006/0100714 | A1 * | 5/2006 | Ensign ................... 623/20.16 |
| 2006/0229615 | A1 * | 10/2006 | Abdou ............... A61B 17/8685 606/256 |
| 2006/0229730 | A1 * | 10/2006 | Railey .................... A61B 17/15 623/21.18 |
| 2008/0103603 | A1 * | 5/2008 | Hintermann ........ A61F 2/4202 623/20.32 |
| 2008/0119934 | A1 | 5/2008 | Eckhardt |
| 2009/0137946 | A1 | 5/2009 | Nassiri et al. |
| 2009/0182433 | A1 * | 7/2009 | Reiley et al. ............. 623/18.11 |
| 2011/0035019 | A1 * | 2/2011 | Goswami et al. ......... 623/21.18 |
| 2011/0153024 | A1 * | 6/2011 | Wagner ................ A61F 2/3804 623/20.12 |
| 2011/0295380 | A1 * | 12/2011 | Long ........................ 623/21.18 |
| 2012/0259338 | A1 | 10/2012 | Carr et al. |
| 2013/0150975 | A1 * | 6/2013 | Iannotti ................ A61F 2/4003 623/19.11 |

FOREIGN PATENT DOCUMENTS

| | | |
|---|---|---|
| FR | 2220235 A1 | 4/1974 |
| JP | H08-501716 A | 2/1996 |
| JP | H11-513274 A | 3/1997 |
| JP | 2004-202232 A | 7/2004 |
| JP | 2004-521685 A | 7/2004 |
| JP | 2004-298638 A | 10/2004 |
| JP | 2008-539922 A | 11/2008 |
| RU | 2062072 C1 | 6/1996 |
| RU | 2145822 C1 | 2/2000 |
| RU | 2149604 C1 | 5/2000 |
| RU | 2155561 C2 | 9/2000 |
| SU | 546349 A1 | 4/1977 |
| SU | 1271509 A1 | 11/1986 |
| SU | 1533685 A1 | 1/1990 |
| WO | 91/07931 A1 | 6/1991 |
| WO | 94/07440 A1 | 4/1994 |
| WO | 97/09939 A1 | 3/1997 |
| WO | 98/07380 A1 | 2/1998 |
| WO | 00/15154 A1 | 3/2000 |
| WO | 01/19294 A1 | 3/2001 |
| WO | 02/067811 A2 | 9/2002 |
| WO | 2007/082810 A2 | 7/2007 |
| WO | 2011/146617 A2 | 11/2011 |

OTHER PUBLICATIONS

International Search Report and Written Opinion issued for International application No. PCT/US2014/031713, dated Sep. 16, 2014, 11 pages.

International Preliminary Report on Patentability issued for International application No. PCT/US2014/031713, dated Sep. 15, 2015, 8 pages.

First Office Action issued for corresponding Chinese patent application No. 201480000395.3, dated Nov. 30, 2016, 8 pages.

Office Action issued for corresponding Canadian patent application No. 2,867,160, dated Nov. 13, 2015, 5 pages.

Office Action issued for corresponding Canadian patent application No. 2,867,160, dated Oct. 17, 2016, 3 pages.

* cited by examiner

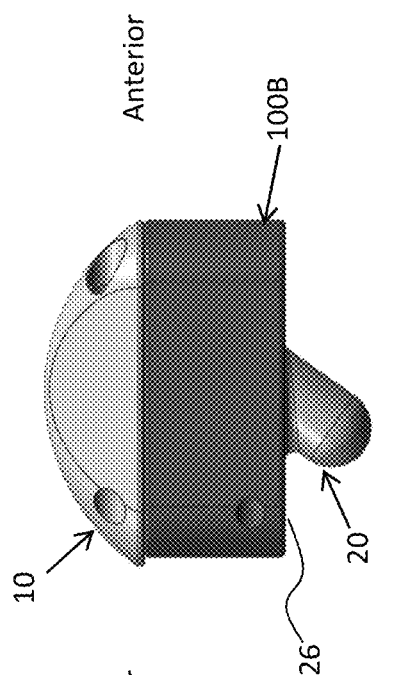
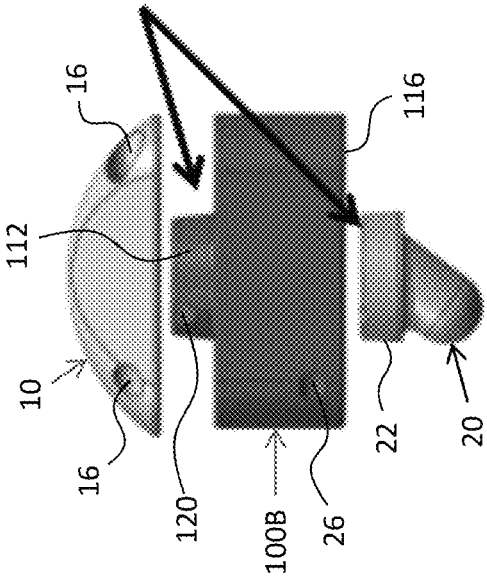
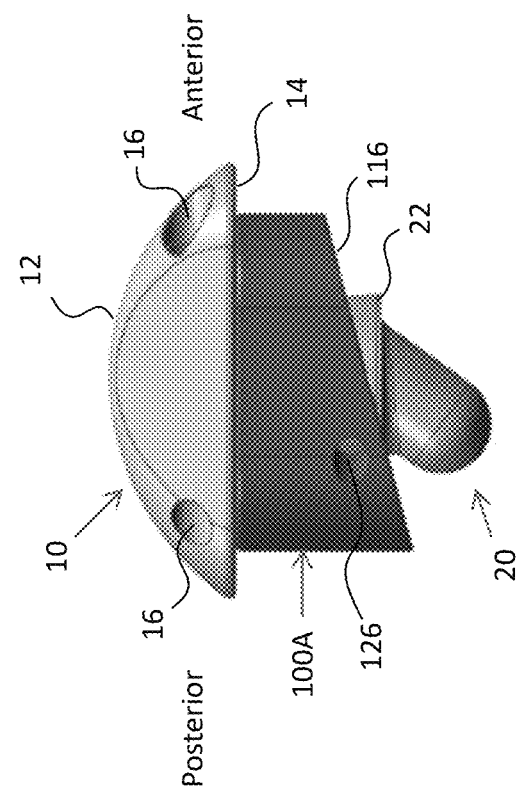
FIG. 5A
FIG. 5B
FIG. 4

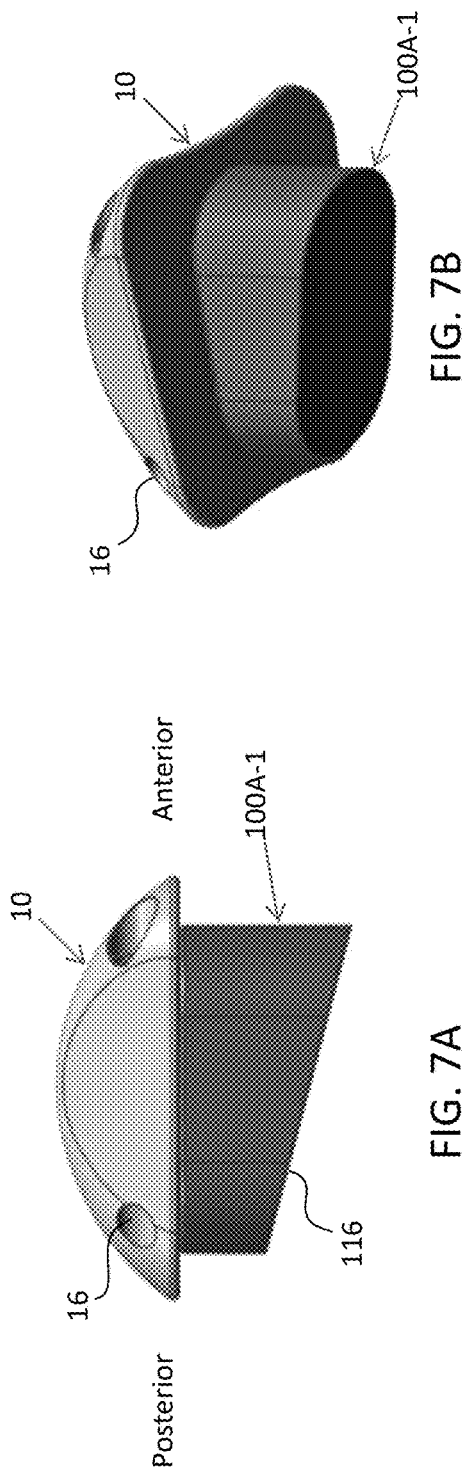
FIG. 7A
FIG. 7B
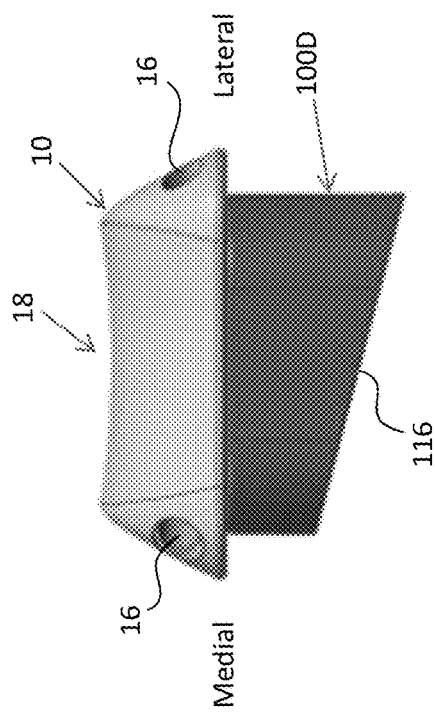
FIG. 8

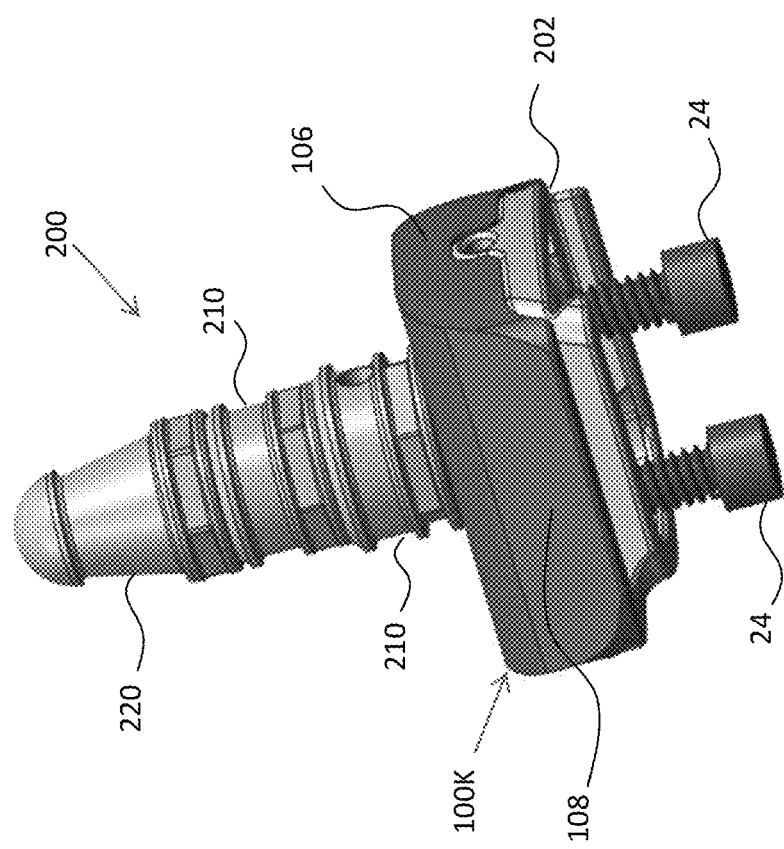

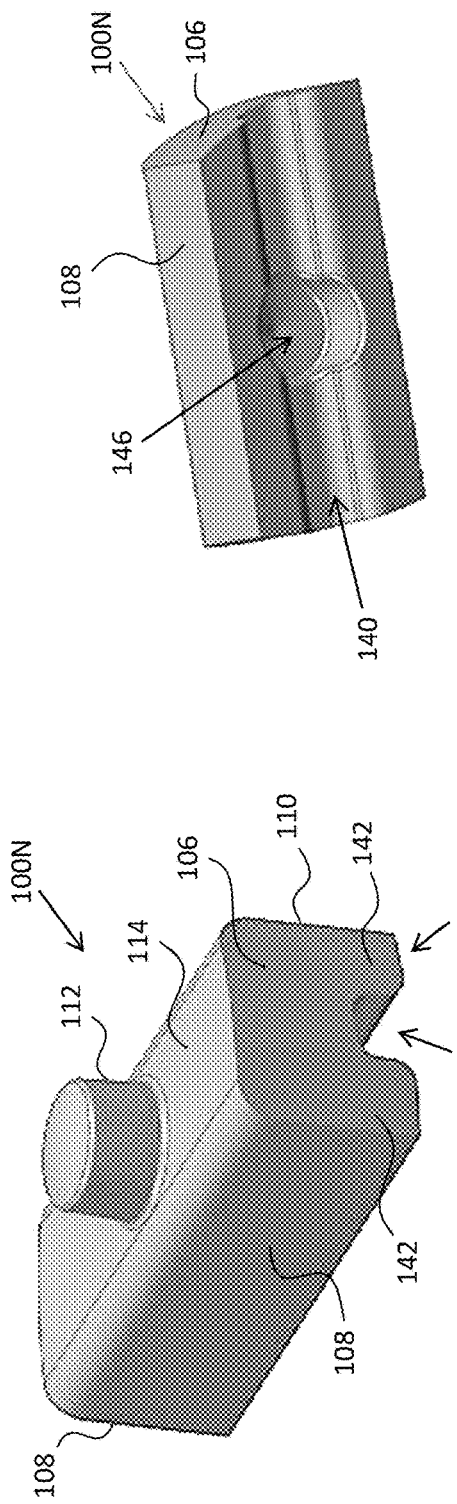
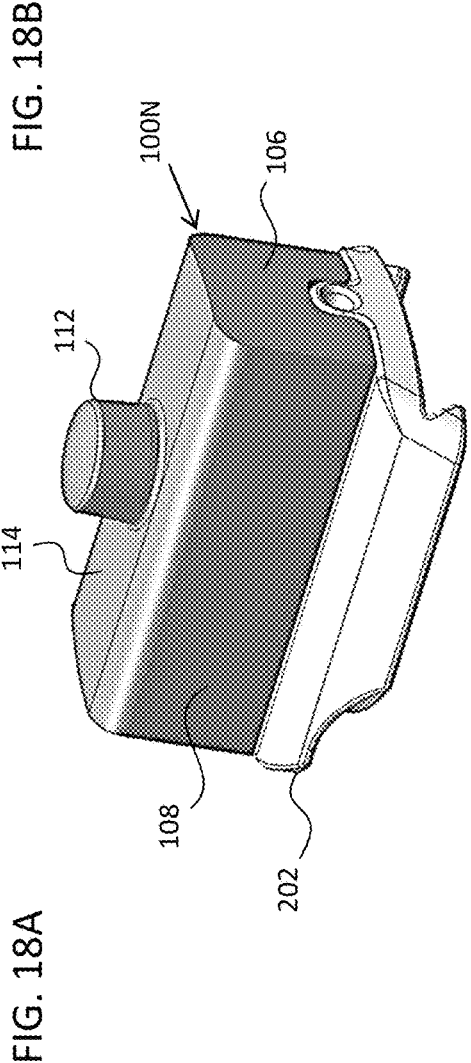
FIG. 18A
FIG. 18B
FIG. 18C

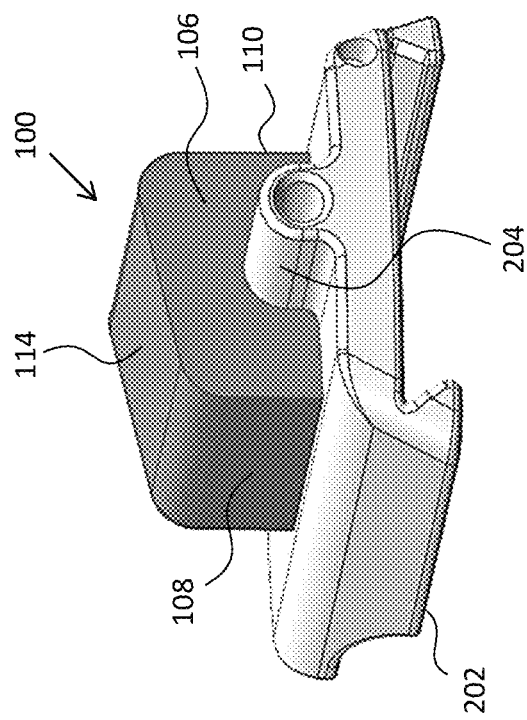
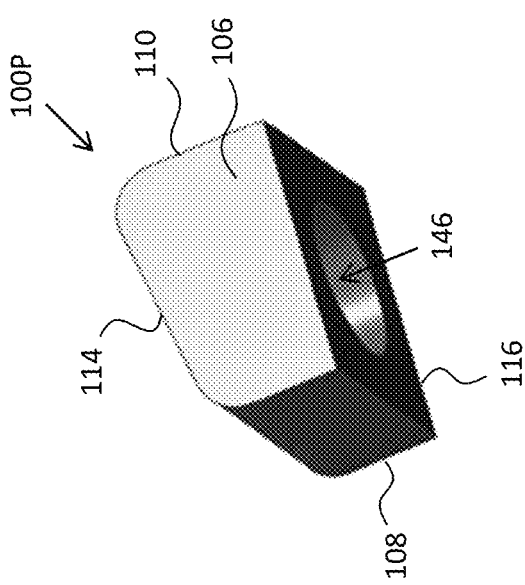
FIG. 19A
FIG. 19B

REVISION IMPLANT AUGMENTS, SYSTEMS, AND METHODS

FIELD OF DISCLOSURE

The disclosed augments, kits, systems, and methods relate to orthopedic implants. More particularly, the disclosed augments, kits, systems, and methods relate to augment inserts for orthopedic implant revisions.

BACKGROUND

Total joint replacements are orthopedic implants for repairing or replacing a natural joint. Examples of common joints that are replaced by a total joint replacement include, but are not limited to, hips, ankles, and shoulders. The ultimate goal with any total joint prosthesis is to approximate the function and structure of the natural, healthy structures that the prosthesis is replacing. In many instances, voids are formed in the patient's bone adjacent to the implant site as a result of osteolysis over a prolonged period of time. These voids can loosen the fixation of the prosthesis within the patient causing greater problems for the patient.

SUMMARY

In some embodiments, a surgical method includes creating an incision in a patient, exposing a multi-component prosthesis implanted in a patient, disassembling at least one component of the multi-component prosthesis, and coupling a first revision implant component to a first component of the multi-component prosthesis. The revision implant component has a body including at least one of a projection or an opening that is complementary to a feature of the first component of the multi-component prosthesis for coupling the revision implant component to the first component of the multi-component prosthesis.

In some embodiments, a revision implant component includes a body including an upper side, a bottom side, and at least one side extending between the upper side and the bottom side. At least one of the upper side and the bottom side includes a feature configured to engage at least one component of a multi-component prosthesis. The shape of the revision implant component is different from each of the components of the multi-component prosthesis.

BRIEF DESCRIPTION OF THE DRAWINGS

FIG. 4 illustrates a revision implant component/augment in accordance with FIGS. 1A and 1B coupled to components of an implant system.

FIGS. 5A and 5B illustrate a revision implant component/augment in accordance with FIGS. 2A and 2B coupled to components of an implant system.

FIGS. 7A and 7B illustrate another example of a revision implant component/augment coupled to a talar dome of an ankle replacement system in accordance with some embodiments.

FIG. 8 illustrates another example of a revision implant component/augment coupled to a talar dome of an ankle replacement system in accordance with some embodiments.

FIG. 15 illustrates another example of a revision implant component/augment coupled to the tibial component of an ankle replacement system using screws.

FIGS. 18A and 18B illustrate another example of a revision implant component/augment in accordance with some embodiments.

FIG. 18C illustrates a revision implant component/augment in accordance with FIGS. 18A and 18B coupled to a tibial platform of a tibial component of an ankle replacement system in accordance with some embodiments.

FIGS. 19A and 19B illustrate another example of a revision implant component in accordance with some embodiments.

DETAILED DESCRIPTION

Figure 1A:
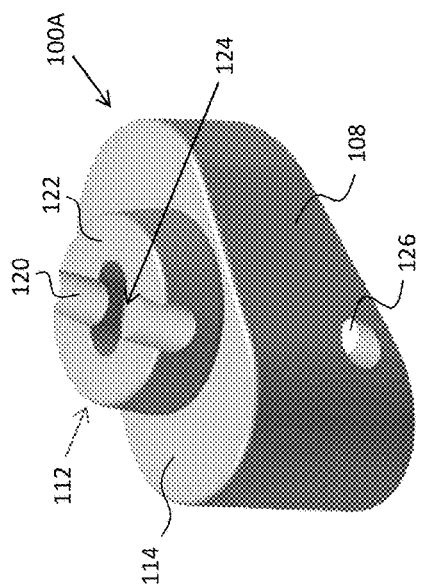
FIG. 1A is an isometric view of the front and underside of one example of a revision implant component in accordance with some embodiments.

This description of the exemplary embodiments is intended to be read in connection with the accompanying drawings, which are to be considered part of the entire written description. The drawing figures are not necessarily to scale and certain features may be shown exaggerated in scale or in somewhat schematic form in the interest of clarity and conciseness. In the description, relative terms such as "horizontal," "vertical," "up," "down," "top" and "bottom" as well as derivatives thereof (e.g., "horizontally," "downwardly," "upwardly," etc.) should be construed to refer to the orientation as then described or as shown in the drawing figure under discussion. These relative terms are for convenience of description and normally are not intended to require a particular orientation. Terms including "inwardly" versus "outwardly," "longitudinal" versus "lateral" and the like are to be interpreted relative to one another or relative to an axis of elongation, or an axis or center of rotation, as appropriate. Terms concerning attachments, coupling and the like, such as "connected" and "interconnected," refer to a relationship wherein structures are secured or attached to one another either directly or indirectly through intervening structures, as well as both movable or rigid attachments or relationships, unless expressly described otherwise. When only a single machine is illustrated, the term "machine" shall also be taken to include any collection of machines that individually or jointly execute a set (or multiple sets) of instructions to perform any one or more of the methodologies discussed herein. The term "operatively connected" is such an attachment, coupling or connection that allows the pertinent structures to operate as intended by virtue of that relationship. In the claims, means-plus-function clauses, if used, are intended to cover the structures described, suggested, or rendered obvious by the written description or drawings for performing the recited function, including not only structural equivalents but also equivalent structures.

The disclosed systems and methods advantageously enable revisions of total ankle implants by providing wedges and block designed to be coupled to the original implant to fill in any gaps formed in the bone from osteolysis. Although the disclosed systems and methods are described with reference to the INBONE total ankle system available from Wright Medical Technology, Inc., of Arlington, Tenn., the disclosed systems and methods can be adapted for other multi-component prosthesis systems.

Figure 1B:
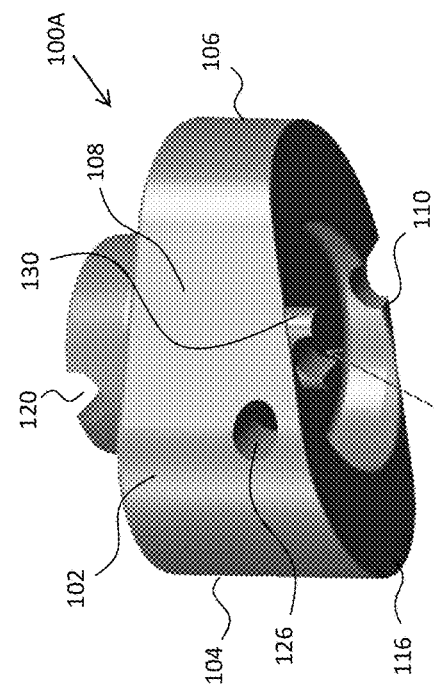
FIG. 1B is an isometric view of the front and top side of the revision implant component/augment illustrated in FIG. 1A.

FIGS. 1A and 1B illustrate one example of a revision implant component 100A in accordance with some embodiments. Referring first to FIG. 1A, revision implant component 100A includes a body 102 having an oblong shape including a first side 104, which is curved, and a second side 106, which is also curved and disposed on the opposite side of body 102 as first side 104. A third side 108 is flat and defines a planar surface and is disposed between first and second sides 104 and 106. A fourth side 110 is also flat and defines a planar surface that is disposed opposite third side 108 and between first and second sides 104, 106. Although revision implant component 100A is described as including a plurality of sides 104, 106, 108, 110 that extend between upper side 114 and bottom side 116, revision implant component 100A includes a single side in the form of a circle, oval, or other continuous shape in some embodiments as will be understood by one of ordinary skill in the art.

A head or protection 112 extends from an upper side 114 and is configured to engage a second revision implant component 100A or a modular stem component of an ankle replacement or other prosthesis system. For example, in some embodiments, head 112 is tapered such that it is configured to form a Morse taper with a corresponding recess of another revision implant component 100A or a modular stem component of an ankle replacement or other implant system. In some embodiments, projection 112 is cylindrical, i.e., not tapered, and includes threads, a bayonet coupling, or other attachment or coupling means for engaging a complementary feature of another revision implant component 100A or a component of an ankle replacement system. Other coupling means for coupling revision implant component 100A to another revision implant component or a component of multi-component prosthesis such as, for example, screws, bolts, or other fasteners can also be used.

Bottom side 116 of revision implant component 100A defines an opening 118 that is sized and configured to be complementary to head 112. For example, if head 112 is tapered, then opening 118 is tapered such the engagement of head 112 within opening 118 forms a Morse taper. In some embodiments when projection 112 is threaded, opening 118 is also threaded. As best seen in FIGS. 1A and 1B, bottom side 116 can be angled (i.e., not parallel) with respect to upper side 114. However, one of ordinary skill will understand that upper side 114 and bottom side 116 are parallel to one another in some embodiments.

Revision implant component 100A also includes features for coupling and uncoupling revision implant component from other revision implant components 100A and/or a component of an ankle replacement or other implant system. For example and as best seen in FIG. 1B, a notch 120 is defined by the top 122 of head 112. In some embodiments, notch 120 has a diameter that is sized and configured to receive a screw driver or other elongate tool therein. As best seen in FIGS. 1A and 1B, notch 120 is disposed at an angle with respect to a plane defined by flat sides 108, 110. In some embodiments, a recess 124 is also defined in the top 122 of head 112.

Hole 126 is defined along sides 108, 110, and in some embodiments at the interface between sides 108, 110 and sides 104, 106, and extends through the body 102. As best seen in FIG. 1A, hole 126 extends through body 102 and cavity 118 such that a notch 128 is defined in protrusion 130, which extends from end surface 132 of cavity 118. The geometry of hole 126 and notch 128 is sized and configured to receive a removal tool, such as a shaft of a screwdriver or dowel, for separating revision implant component 100A from an engagement with another revision implant component or a component of an ankle replacement system.

Figure 2A:
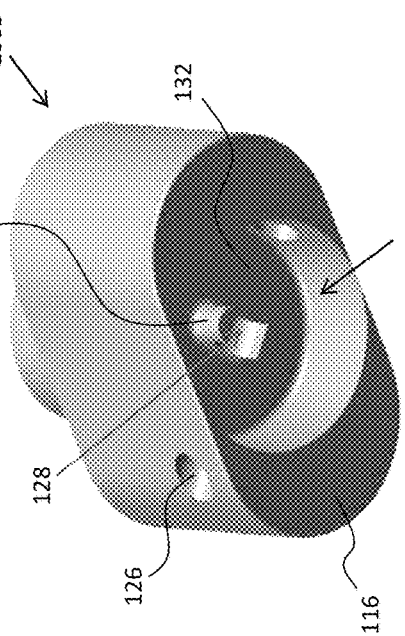
FIG. 2A is an isometric view of the front and top side of another example of a revision implant component/augment.
Figure 2B:
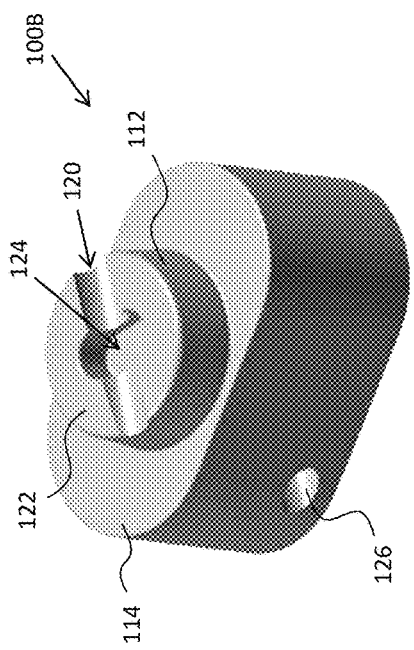
FIG. 2B is a bottom side isometric view of the revision implant component/augment illustrated in FIG. 2A.

As will be understood by one of ordinary skill in the art, the size and shape of revision implant components/augments can be varied. For example, FIGS. 2A and 2B illustrate another example of a revision implant component 100B in accordance with some embodiments. The embodiment of a revision implant component 100B illustrated in FIGS. 2A and 2B is similar to the embodiment illustrated in FIGS. 1A and 1B except that a plane defined by upper side 114 is parallel to a plane defined by bottom side 116.

Figure 3B:
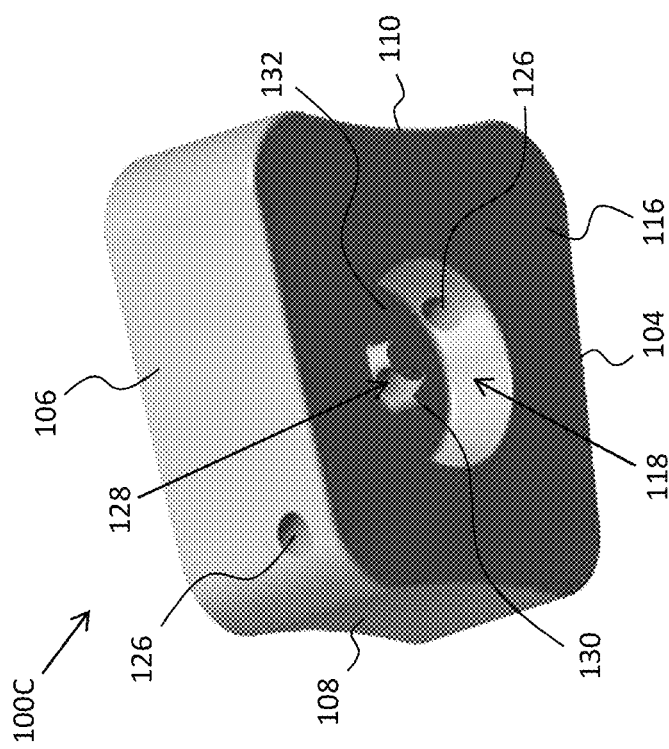
FIGS. 3A and 3B illustrate different view of another example of a revision implant component/augment.
Figure 3A:
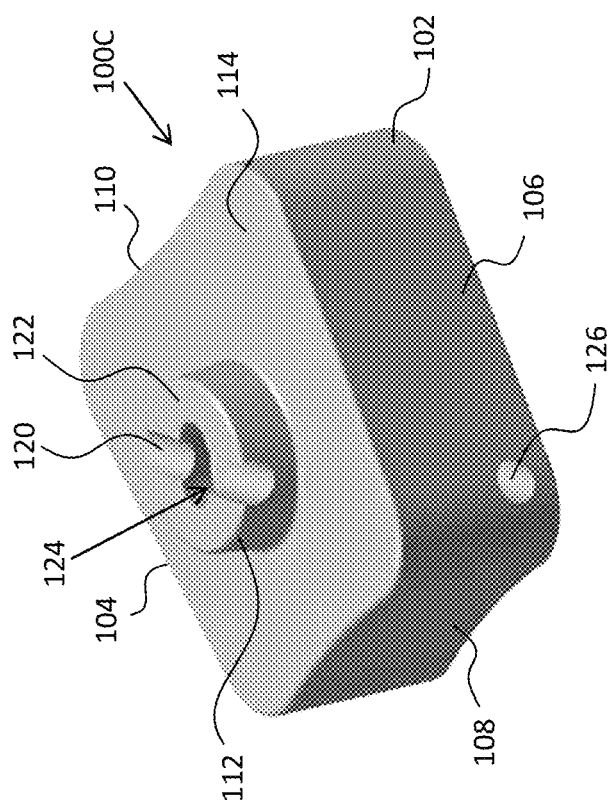

Referring now to FIGS. 3A and 3B, another example of a revision implant component 100C is illustrated including a body 102 having sides 104, 106, 108, and 110. Sides 108 and 110 have a concave curvature (best seen in FIG. 3B) and sides 104 and 106 being substantially flat and each defining a substantially planar surface. In some embodiments, the interfaces between adjacent sides 104, 106, 108, 110 can be rounded, although one of ordinary skill in the art will understand that the interfaces could be pointed or chamfered.

A head or projection 112 extends from an upper side 114 and is configured to engage a second revision implant component 100B or a component of an ankle replacement or other implant system. As described above, head 112 can be tapered such that it is configured to form a Morse taper with a corresponding recess of another revision implant component 100 or a component of an ankle replacement or other implant system in some embodiments. However, head 112 can also be implemented a threaded cylinder or include other attachment means for engaging a complementary feature of another revision implant component 100 or a component of an ankle replacement or other implant system.

An opening 118 sized and configured to be complementary to head 112 is defined by bottom side 116 of revision implant component 100C. For example, if head 112 is tapered, then opening 118 is tapered such the engagement of head 112 within opening 118 forms a Morse taper. If, for example, projection 112 is threaded, opening 118 is also threaded.

In some embodiments, head 112 defines a notch 120 in its top surface 122. Notch 120 is sized and configured to receive a screw driver or other elongate tool therein for separating revision implant component from another revision implant component or from a component of an implant component. As best seen in FIG. 3A, notch 120 is disposed at an angle such that an axis defined by notch 120 extends diagonally across body 102. In some embodiments, a recess 124 is also defined in the top 122 of head 112. Notch 124 assists a surgeon or other medical professional in orienting the Morse Taper for coupling with another revision implant component/augment or with a component of a multi-component ankle prosthesis.

A hole 126 is defined along sides 104, 106, and in some embodiments at the interface between sides 108, 110 and sides 104, 106. As best seen in FIG. 3B, hole 126 extends through the body 102 and intersects cavity 118. When cavity 118 includes a protrusion 130 extending toward bottom surface 116 from cavity end surface 132, hole 126 forms a notch 128 in protrusion 130. The geometry of hole 126 and notch 128 is sized and configured to receive a removal tool, such as a shaft of a screwdriver or dowel, for separating revision implant component 100C from an engagement with another revision implant component or a modular stem component of an ankle replacement system.

The revision implant components 100A, 100B, 100C described above can be coupled together or to components of an ankle replacement or other implant system. For example, FIG. 4 illustrates a revision implant component 100A coupled between a talar dome 10 and a stem 20 of an ankle replacement system. Talar dome 10 includes a convex or saddle-shaped upper surface 12 and has a bottom surface 14 that defines an opening (not shown) that is sized and configured to receive enlarged and tapered head 22 of stem 20 and head 112 of revision implant component 100A. In some embodiments, talar dome 10 defines one or more holes 16 in upper surface 12 of dome 10. Hole(s) 16 are sized and configured to receive a removal tool such as, for example, a screwdriver or dowel. At least one of hole(s) 16 aligns with notch 120 defined by head 112 of revision implant component 100A.

FIGS. 5A and 5B illustrate a revision implant component 100B coupled to a talar dome 10 and a stem 20 (FIG. 5A) and an exploded view of the same (FIG. 5B). The arrows in FIG. 5B identify that the geometry enlarged and tapered head 22 of stem 20 and head 112 of revision implant component 100B are similar to each other such that the tapered head 22 of stem 20 and the tapered head 112 of revision implant component 100B are both configured to lock to talar dome 10.

Figures 6A, 6B:
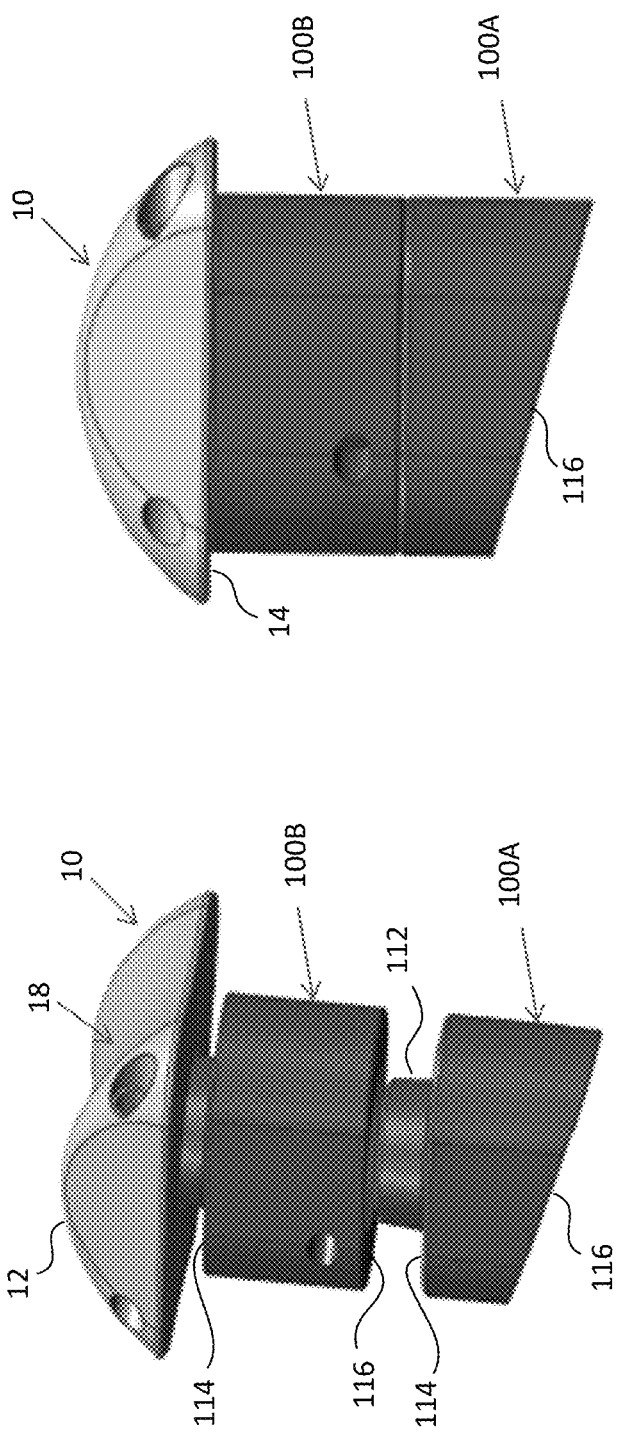
FIGS. 6A and 6B illustrate a pair of revision implant components/augments in accordance with FIGS. 1A-2B coupled to a talar dome of an ankle replacement system in accordance with some embodiments.

Turning now to FIGS. 6A and 6B, a talar dome 10 is illustrated being coupled to a pair of revision implant components 100A and 100B. Revision implant component 100A includes a bottom side 116 that defines a plane that is parallel to a plane defined by upper side 114, and revision implant component 100B includes a bottom side 116 that defines a planar surface that is disposed at an angle (i.e., a non-zero degree angle) with respect to a plane defined by upper side 114. As best seen in FIG. 6A, the upper surface 12 of talar dome 10 is saddle shaped with an inwardly extending depression 18. The depression 18 defines an articulating surface extending in an anterior-posterior direction, which is the same direction in which the angle opens between bottom side 116 and upper side 114 opens in FIG. 6A.

In some embodiments, such as the embodiment illustrated in FIGS. 7A and 7B, the bottom side 116 of revision implant component 100A-1 does not define a cavity 118 for receiving a head 112 of another revision implant component 100, a tapered head 22 of a stem 20, or a taper of another prosthesis implant component. Revision implant component 100A-1 can be secured within an intramedullary cavity using bone cement, screws, other fixation means, or combinations thereof.

The direction that the angle between bottom surface 116 and upper surface 114 faces can be non-parallel to anterior-posterior direction. For example and as illustrated in FIG. 8, the direction in which the angle between bottom side 116 and upper side 114 of revision implant component 100D is parallel to the medial-lateral direction. The angle of bottom face 116 can vary in position when related to implant 10 as illustrated in FIGS. 7A, 7B, and 8.

Figure 9B:
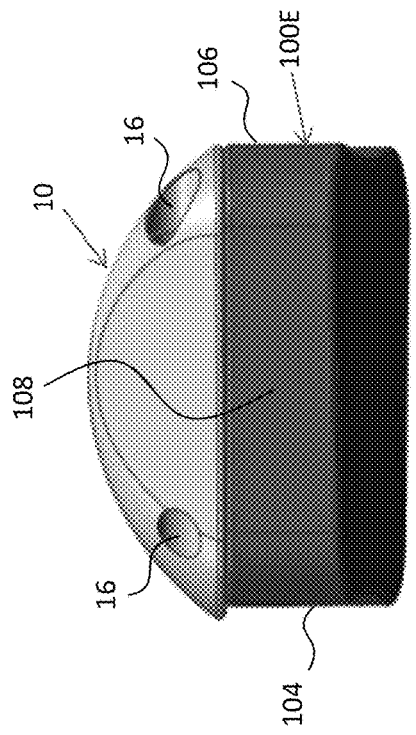
FIGS. 9A and 9B illustrate another example of a revision implant component/augment coupled to a talar dome of an ankle replacement system in accordance with some embodiments.
Figure 9A:
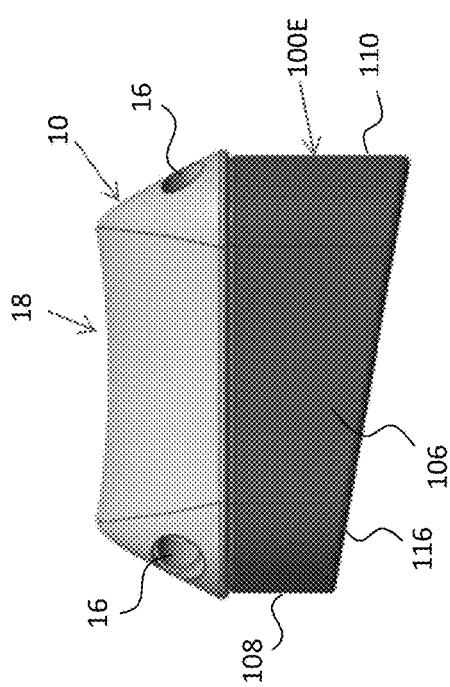

The physical dimensions and geometry of the revision implant components can be varied. For example, FIGS. 9A and 9B illustrate an embodiment of a revision implant component 100E having length and width dimensions that approximately correspond to the length and width dimensions of talar dome 10. Revision implant component 100E is illustrated as having a planar surface defined by bottom side 116 that is disposed at an angle with respect to a planar surface defined by upper side 114, which is shown as being in abutment with the underside 14 of talar dome 10. However, as described above, a planar surface defined by bottom side 116 may also be disposed such that it is parallel to a planar surface defined by upper side 114. Sides 104, 106, 108, 110 of revision implant component 100E are disposed approximately perpendicular to a plane defined by upper side 114.

Figure 10B:
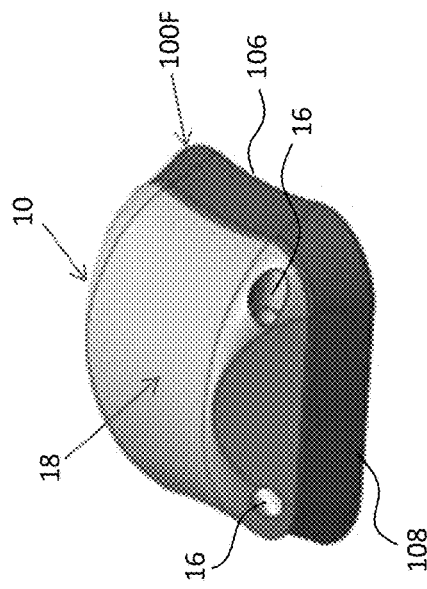
FIGS. 10A and 10B illustrate another example of a revision implant component/augment coupled to a talar dome of an ankle replacement system in accordance with some embodiments.
Figure 10A:
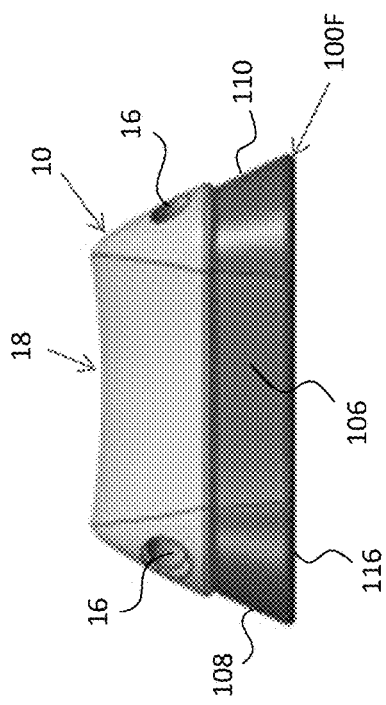

In some embodiments, such as the embodiment illustrated in FIGS. 10A and 10B, sides 104, 106, 108, 110 are disposed at angles, other than perpendicular angles, with respect to the plane defined by upper side 114. As best seen in FIG. 10A, sides 104, 106, 108 110 are angled such that the length and width of bottom side 116 are greater than the length and width of upper side 114. In some embodiments, sides 104, 106, 108, 110 are angled such that upper side 114 has a greater length and width dimension that bottom side 116. As best seen in FIG. 10B, sides 104, 106, 108, 110 can be concave such that a smooth transition is provided between talar dome 10 and revision implant component 100F.

Figure 11A:
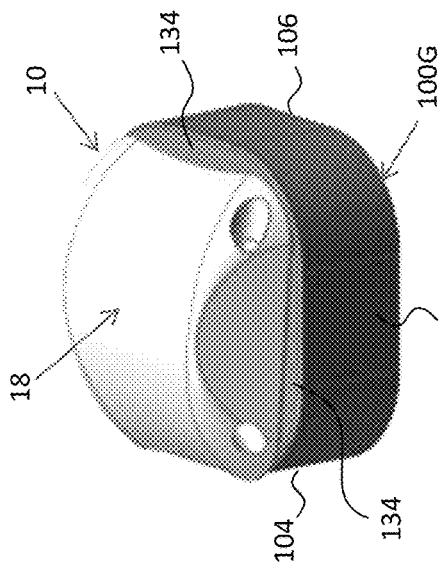
FIGS. 11A and 11B illustrate another example of a revision implant component/augment coupled to a talar dome of an ankle replacement system in accordance with some embodiments.
Figure 11B:
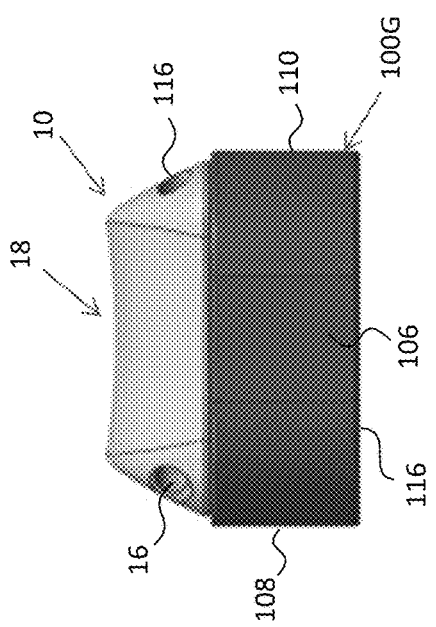

Turning now to FIGS. 11A and 11B, which illustrate another embodiment in accordance with the present disclosure, revision implant component 100G includes sides 104, 106, 108, 110 extending in a substantially perpendicular direction from a planar surface defined by upper side 114. The length and width of upper side 114 and bottom side 116 are greater than the length and width dimensions of talar dome 10 such that upper side 114 includes areas 134 that extend beyond the boundaries of talar dome 10 as best seen in FIG. 11B.

Figure 12A:
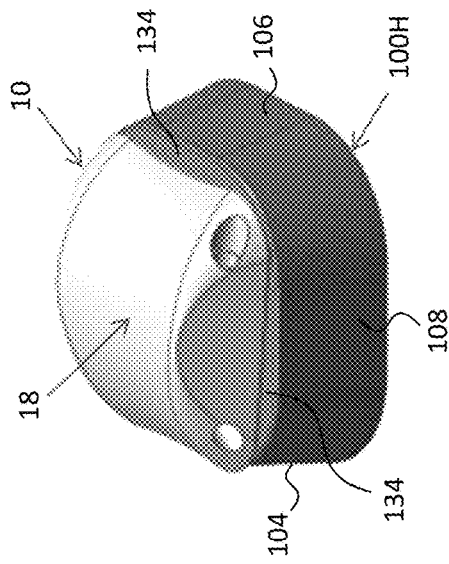
FIGS. 12A and 12B illustrate another example of a revision implant component/augment coupled to a talar dome of an ankle replacement system in accordance with some embodiments.
Figure 12B:
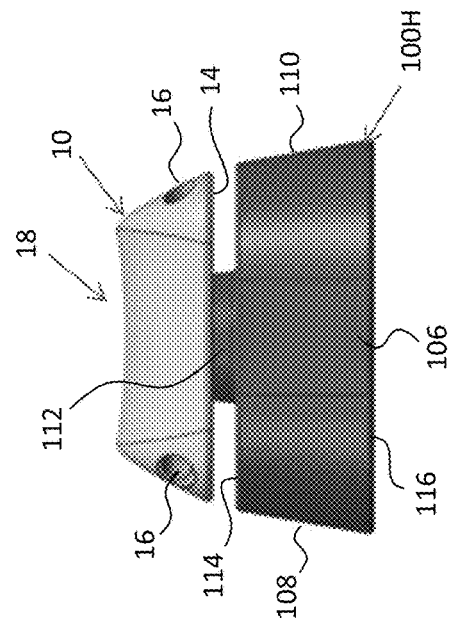

FIGS. 12A and 12B illustrate another embodiment of a revision implant component 100H in which the length and width of upper side 114 and bottom side 116 are greater than the length and width dimensions of talar dome 10 such that areas 134 extend beyond the boundaries of talar dome 10. Sides 104, 106, 108, 110 are angled such that the length and width of bottom side 116 are greater than the length and width of upper side 114. In FIG. 12A, the tapered head 112 can be seen between the bottom surface 14 of talar dome 10 and the upper side 114 of revision implant component 100H.

Figure 13:
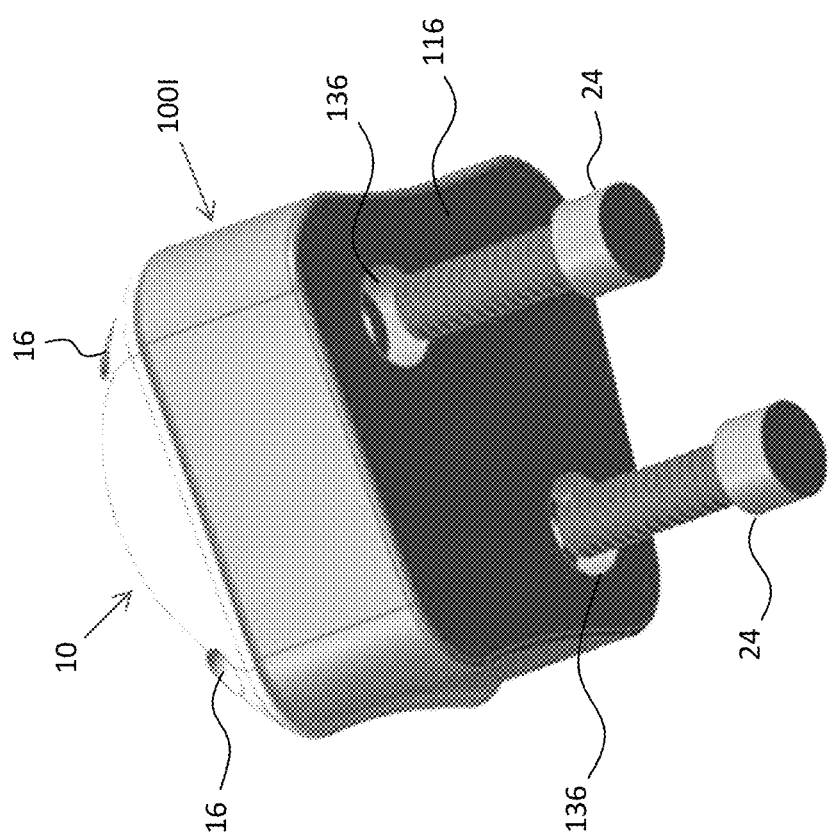
FIG. 13 illustrates another example of a revision implant component/augment coupled to a talar dome of an ankle replacement system using screws in accordance with some embodiments.

FIG. 13 illustrates an embodiment of a revision implant component 100I in which screws are used to lock the revision implant component 100I to a talar dome 10. As shown in FIG. 13, bottom side 110 of revision implant component 100I defines countersunk holes 136 that are sized and configured to receive screws 24 therein. Although not visible in FIG. 13, talar dome 10 includes threaded holes that align with countersunk holes 136 of revision implant component 100I.

Figure 14C:
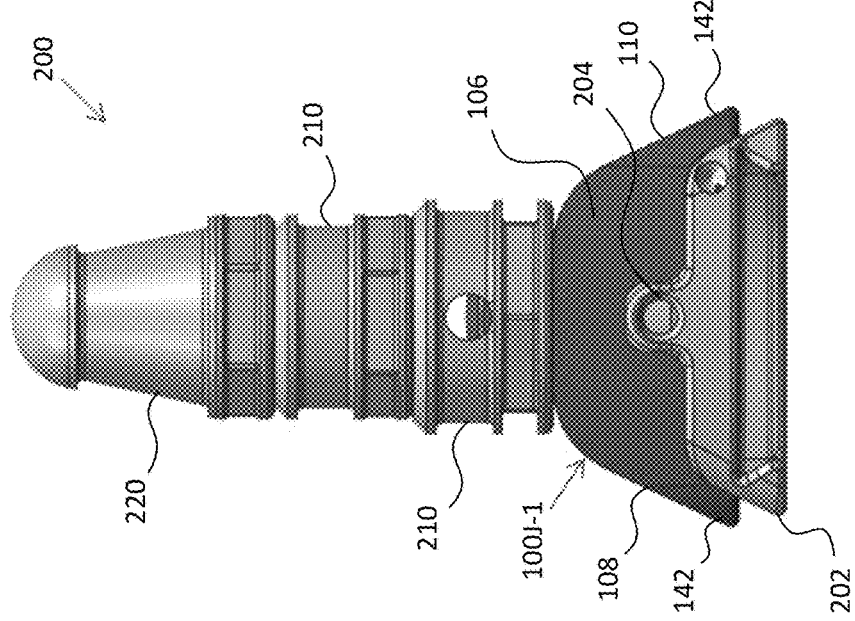
FIG. 14C illustrates a revision implant component/augment similar to the revision implant component/augment illustrated FIGS. 14A and 14B coupled to the tibial component of an ankle replacement system.
Figure 14A:
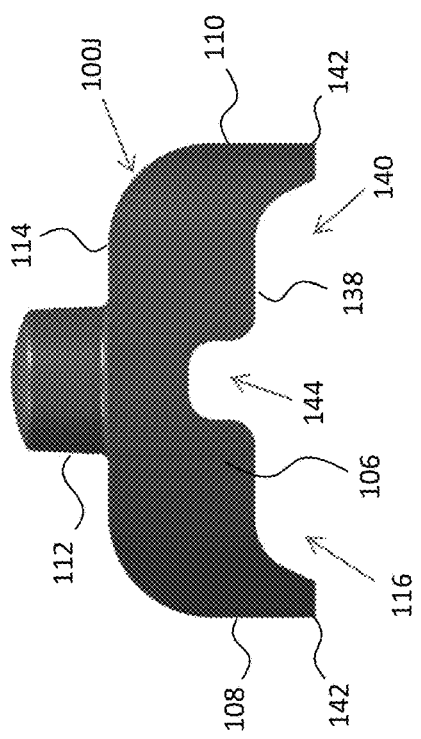
FIGS. 14A and 14B provide different views of another example of a revision implant component/augment in accordance with some embodiments.
Figure 14B:
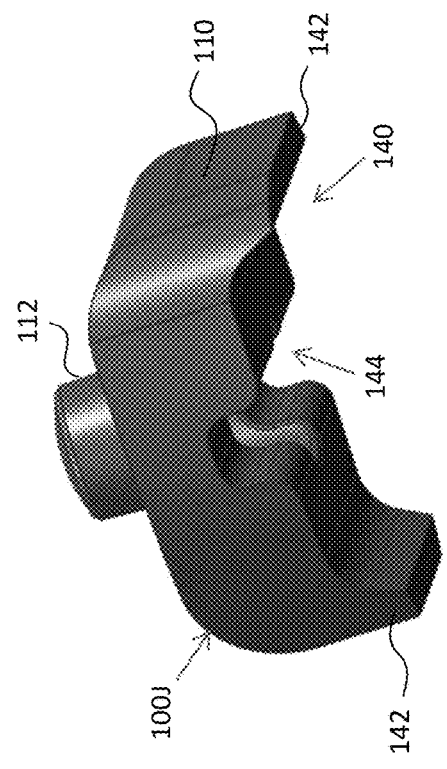

As described above, the geometry of the revision implant components can vary such that a revision implant component has a geometry that is complementary to other implant components or to the geometry to the intramedullary channels or cavities. For example, FIGS. 14A-14C illustrate one example of such a revision implant component 100J configured for use with a tibial implant of an ankle replacement system. The bottom side 116 of revision implant component 100J includes a contoured surface 138 that complements the upper surface of a tibial platform 202 of a tibial stem component 202 of the ankle replacement system 200, which is illustrated as an ankle replacement system in accordance with the system described in U.S. patent application Ser. No. 12/410,978, filed Mar. 25, 2009, the entirety of which is herein incorporated by reference.

Contoured surface 138 defines a channel 140 that extends inwardly between legs 142. A groove 144 inwardly extends from the approximate midpoint of channel 140 and is sized and configured to receive raised alignment guide 204 of tibial platform 202 as best sent in FIG. 14C. A tapered head 112 extends from the upper side 114 of revision implant component 100J and is sized and configured to be received within a complementary opening defined by a prosthesis stem component, such as an intermediate stem component 210 or end stem component 220 of ankle prosthesis 200.

FIG. 15 illustrates an embodiment of a revision implant component 100K that is configured to be coupled to tibial platform 202 of ankle implant system 200 via screws 24. Although not visible in FIG. 15, revision implant component 100K includes a tapered head 112 extending from upper side 114 that engages intermediate component via a taper lock. Bottom side 116 includes contoured surface 138 that complements the upper surface of a tibial platform 202 of a tibial implant 200 like contoured surface 138 of revision implant component 100J illustrated in FIGS. 14A-14C.

Figure 16C:
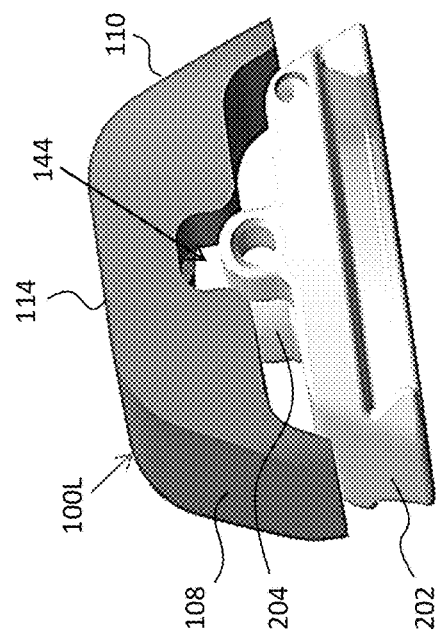
FIG. 16C illustrates a revision implant component/augment in accordance with FIGS. 16A and 16B coupled to a tibial platform of a tibial component of ankle replacement system in accordance with some embodiments.
Figure 16A:
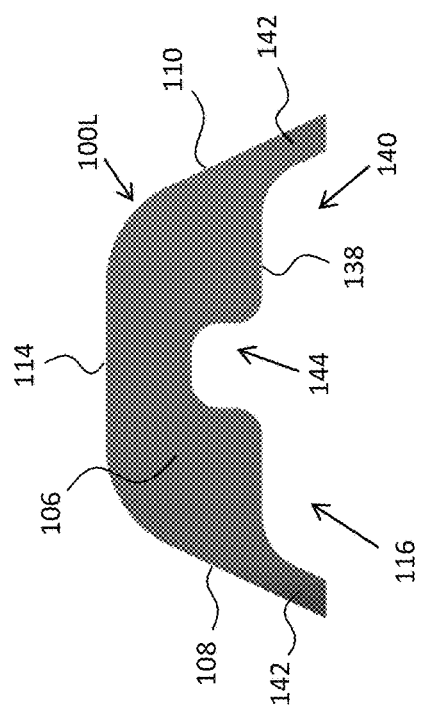
FIGS. 16A and 16B provide different views of another example of a revision implant component/augment in accordance with some embodiments.
Figure 16B:
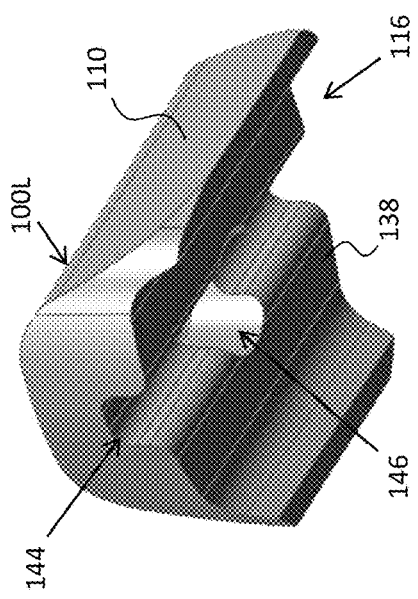

In some embodiments, such as the embodiments illustrated in FIGS. 16A-16D, revision implant component 100L is configured as a spacer for insertion between implant components. As shown in FIG. 16A, revision implant component 100L has a similar shape to the shape of revision implant component 100K except that revision implant component 100L does not include a tapered head 112 extending from the upper side 114. In FIG. 16B, a hole 146 is shown at the approximate middle of groove 144 and extends through revision implant component 100L. Hole 146 is sized and configured to receive tapered head 204 of tibial platform 202 (FIG. 16C) in either a taper-locking engagement or in a non-locking engagement.

Figure 16D:
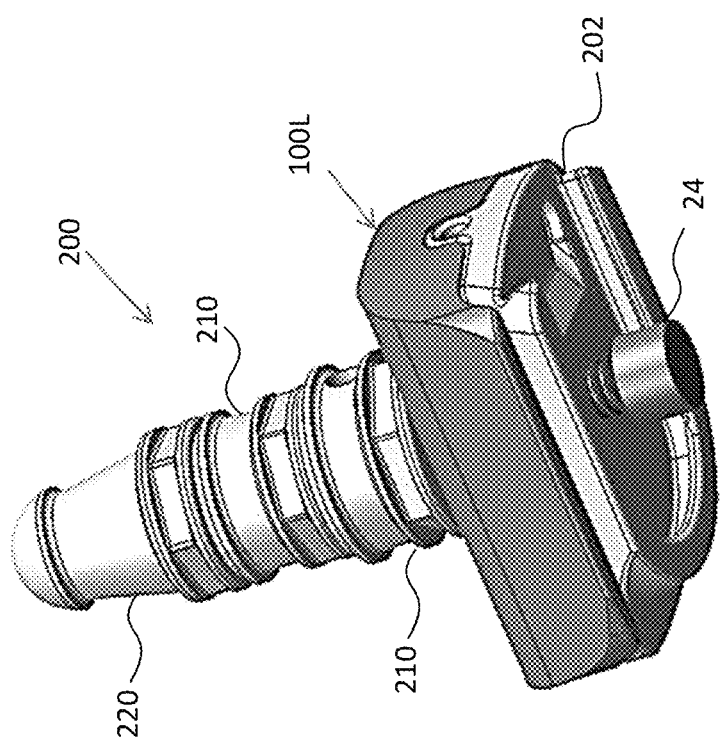
FIG. 16D illustrates another example of a revision implant component/augment coupled to the tibial component of an ankle replacement system using a screw.

As shown in FIG. 16D, a screw 24 is used to secure tibial platform 202 to revision implant component 100L and to intermediate implant component 210 of ankle replacement system 200. For example, screw 24 passes through tibial platform 202 and revision implant component 100L and engages threads of a threaded hole (not shown) defined by intermediate implant component 210. Although a socket head screw 24 is illustrated, other screw types are possible including, but not limited to, pan head and flat head screws, to list but only a couple possible screw types.

Figure 17B:
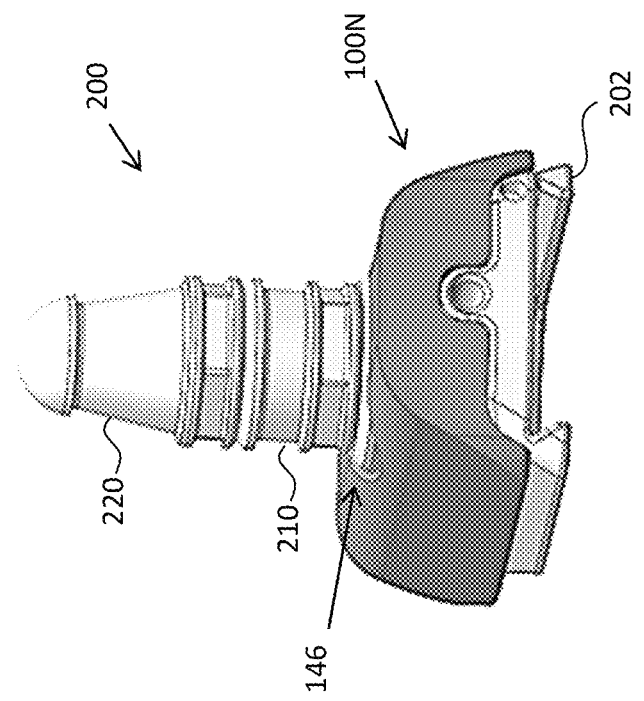
FIGS. 17A and 17B illustrate another example of a revision implant component/augment surrounding a tibial platform of a multi-component tibial prosthesis.
Figure 17A:
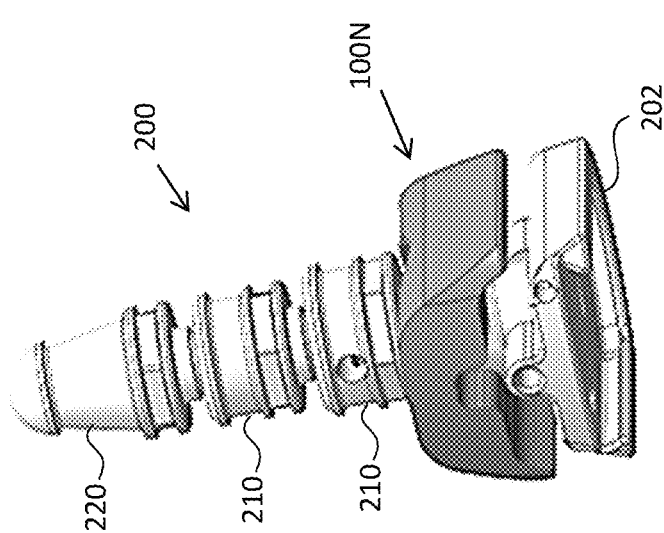

FIGS. 17A and 17B illustrate another example of a revision implant component 100N in which opening 146 defined by body 102 is sized and configured to receive an intermediate implant component 210 therein. In some embodiments, hole 146 is sized to provide a slip fit or a friction fit to an intermediate implant component 210.

FIGS. 18A-18C illustrate another example of a revision implant component 100N configured to be coupled to a tibial platform 202 and/or to other components of a multi-component implant. Revision implant component 100N is shaped as a rectangular prism includes sides 104, 106, 108, 110 that extend perpendicularly from bottom side 116 and upper side 114. A tapered head 112 extends from upper side 112 and is sized and configured to engage another revision implant component or a replacement prosthesis component.

Bottom side 116 define a channel 140 that extends in a longitudinal direction across revision implant component 100N such that revision implant component 100N includes a pair of legs 142. As best seen in FIG. 18B, a blind hole 146 is defined at the approximate middle of channel 140. Blind hole 146 is sized and configured to receive a tapered head 114 of another revision implant component or a tapered head of an implant system, such as a tibial platform 202 of an ankle replacement system 200 as illustrated in FIG. 18C. As shown in FIG. 18C, channel 140 is sized and configured to receive raised alignment guide 204 of tibial platform 202.

FIGS. 19A and 19B illustrate another example of a revision implant component 100P, which includes an upper side 114 that is disposed at an angle with respect to bottom side 116. Unlike revision implant component 100N, upper side 114 of revision implant component 100P does not include a tapered head extending from upper side 114, and bottom side 116 does include a channel 140. In some embodiments, bottom side 116 define a hole 146 sized and configured to receive a tapered head of another revision implant component or prosthesis component therein. In some embodiments, hole 146 can be omitted. As shown in FIG. 19B, revision implant component 100P includes a channel 140 defined by bottom side 116 that is sized and configured to receive a raised alignment guide 204 of a tibial platform 202.

As described above, the revision implant components/augments can have a variety of shapes and geometries. In some embodiments, the revision implant components/augments are formed from a plasma sprayed titanium, although other materials including, but not limited to, BIOFOAM®, available from Wright Medical Technology, Inc., and other metal, ceramic, plastic, and bone growth materials.

The size and shape of the revision implant component/augment 100 can be selected after pre-operative assessment using fluoroscopy to identify the position of a multi-component prosthesis that is implanted in bone, or the selection of the appropriate revision implant component/augment 100 can be performed intraoperatively by a surgeon or other healthcare provider after reviewing the implant site. In some embodiments, the revision implant components/augments 100 are individually sterilized and packaged while in some embodiments the implant components/augments 100 are provided in a kit. For example, when provided in a kit, each individual implant component/augment 100 may be individually packaged and included in a larger container or packaging. However, kits can also be formed without packing multiple implant components/augments 100 in a single package.

During a revision operation, a multi-component prosthesis that was previously implant in a patient may be partially or completely disassembled. For example, if the multi-component implant is a multi-component tibial prosthesis 200 including a tibial platform 202, one or more intermediate components 210, and an end component 220, then the surgeon can decouple the tibial platform 202 and/or one or more intermediate components 210 using a tool such a screw driver, a dowel, or a specialized instrument as will be understood by one of ordinary skill in the art. For example, a tibial platform 202 can be separated from an intermediate implant component 210 by disengaging the Morse taper or unscrewing the implant components 202, 210. If, for example, the multi-component prosthesis is a talar prosthesis, then the talar dome 10 can be decoupled from talar stem 20 by disengaging the Morse taper coupling. When completely disassembled, the entire multi-component prosthesis is removed from the patient.

With the multi-component implant at least partially disassembled, one or more revision implant components/augments 100 are assembled to the multi-component prosthesis in situ using the applicable attachment mechanism. In some embodiments, the in situ attachment includes inserting one or more revision implant components/augments 100 into a pre-existing intramedullary cavity and attaching the revision implant components/augments 100 to the implanted component(s) of the multi-component prosthesis. It is also possible to couple together one or more revision implant components/augments 100 with one or more components of the multi-component prosthesis ex situ and then couple the resulting assemblage to any components of the multi-component prosthesis. For example, if the multi-component implant is completely removed from the patient, the surgeon or another medical professional or care giver can implant one or more components of a multi-component prosthesis with one or more revision implant components/augments 100.

As described above, the revision implant components/augments can have different shapes from each other and/or from the shapes of the components of the multi-component prosthesis such that the revision implant components/augments 100 can be coupled together to fill a void in a bone. Additionally, a single revision implant component/augment can include multiple attachment means such as, for example, a taper, threads, a bayonet coupling, to list but only a few possibilities.

Although the devices, kits, systems, and methods have been described in terms of exemplary embodiments, they are not limited thereto. Rather, the appended claims should be construed broadly, to include other variants and embodiments of the devices, kits, systems, and methods, which may be made by those skilled in the art without departing from the scope and range of equivalents of the devices, kits, systems, and methods.

What is claimed is:

1. A prosthesis, comprising:
   a tibial stem configured to be inserted longitudinally into a tibia, the tibial stem having a tapered first opening;
   a monolithic revision implant body attachable to the tibial stem, including an upper side, a bottom side, and a first leg and a second leg having opposed first and second sides, respectively, each of the first and second sides extending between the upper side and the bottom side, each of the first leg and the second leg having a respective flat end surface at an end thereof opposite from the upper side,
   wherein the upper side has a planar surface, the flat end surfaces are parallel to the planar surface, the bottom side includes smoothly contoured surfaces that define a channel between the first leg and the second leg, the channel having a pair of flat channel surfaces between contoured surfaces and a single groove midway between the flat channel surfaces, wherein the groove extends into the bottom side of the channel from an approximate midpoint of the channel, and wherein the bottom side defines a second opening extending inwardly from the bottom side at an approximate midpoint within the channel and the groove,
   wherein the channel and the groove extend from the first side to the second side such that the channel and the groove extend through the body, and
   wherein a protrusion extends from the upper side of the body and is configured with a tapered surface to engage the first opening in the tibial stem to form a Morse taper seal between the revision implant and the tibial stem; and
   a detachable tibial platform received by the channel of the revision implant body, the tibial platform having an alignment guide sized and shaped to be received by the bottom side of the revision implant body, the tibial platform having a flat bottom surface opposite the alignment guide and a pair of side members attached to the bottom surface.

2. The prosthesis of claim 1, wherein the alignment guide is shaped to fit within the groove while a top surface of the tibial platform is received in the channel.

3. The prosthesis of claim 1, wherein the second side of the monolithic revision implant body is separated from the first side of the monolithic revision implant body by a third side and a fourth side.

4. The prosthesis of claim 3, where the third side and the fourth side extend between the upper side and the bottom side of the monolithic revision implant body in a non-parallel relationship.

5. The prosthesis of claim 4, wherein the second opening has a circular cross-sectional shape.

6. The prosthesis of claim 1, wherein the monolithic revision implant body is formed from a single piece of a material.

7. The prosthesis of claim 6, wherein the monolithic revision implant body is formed from plasma sprayed titanium.

* * * * *